United States Patent [19]

Koashi et al.

[11] Patent Number: 4,883,953

[45] Date of Patent: Nov. 28, 1989

[54] SPECTROSCOPIC METHOD AND APPARATUS FOR MEASURING SUGAR CONCENTRATIONS

[75] Inventors: Katsue Koashi, Toyonaka; Hiroshi Yokota, Sakai, both of Japan

[73] Assignee: Kurashiki Boseki Kabushiki Kaisha, Okayama, Japan

[21] Appl. No.: 267,109

[22] Filed: Nov. 1, 1988

[30] Foreign Application Priority Data

Nov. 17, 1987 [JP] Japan .................................. 62-290821

[51] Int. Cl.⁴ .......................................... G01J 3/50
[52] U.S. Cl. .................................. 250/226; 356/320
[58] Field of Search .................... 250/226, 231 R, 228; 356/319, 320, 321

[56] References Cited

U.S. PATENT DOCUMENTS

| | | | |
|---|---|---|---|
| 4,645,922 | 2/1987 | Welbourn et al. | 250/226 |
| 4,655,225 | 4/1987 | Dahne et al. | 128/663 |
| 4,755,048 | 7/1988 | Kaufman | 356/320 |

*Primary Examiner*—David C. Nelms
*Attorney, Agent, or Firm*—Wenderoth, Lind & Ponack

[57] ABSTRACT

This disclosure relates to a method for measuring the concentrations of sugars in liquids by the use of near infrared as well as an apparatus for practicing said method.

The method comprises a step wherein the absorption spectrum of the sugar under investigation existing at a first depth relatively close to the surface in a sample is computed by using relatively weak power of near infrared, a step wherein the absorption spectrum of the sugar under investigation existing at a relatively deep second depth in the sample is computed by using relatively strong power of infrared, and a step wherein the concentration of the sugar under investigation in the sample is determined by computing the absorption spectrum of the sugar at a different depth between said first and second depths on the basis of the results of measurement in said first and second steps. The wavelengths for the use for said absorption spectrum are selected from anyone of wavelength bands of 950–1,150 nm, 1,150–1,300 nm, and 1,300–1,450 nm.

Since, according to this method, wavelengths which are shorter and closer to the visible region than in the prior art are used, the method enables the measuring light beams to penetrate deeper in a living tissue and makes it possible to measure the concentrations of sugars existing in a deeper region non-invasively.

5 Claims, 7 Drawing Sheets

SPECTROSCOPIC METHOD AND APPARATUS FOR MEASURING SUGAR CONCENTRATIONS

BACKGROUND OF THE INVENTION

1. Field of the invention

The present invention relates to a spectroscopic method for measuring the concentrations of sugars such as glucose, saccharose, fructose and the like and, more particularly, to a method and apparatus for measuring sugar concentrations in foods, fruits and other agricultural products, and the like and in body fluids of man, animals, and other creatures by a non-invasive or non-destructive and easily repeatable technique, that is, without taking the sugar medium as sample for measurement out of the object of examination.

2. Related art

A non-invasive and easily repeatable measuring method as mentioned above is specially useful in that the method dispenses with the step of taking a sample, for example the body fluid, out of the object of examination in the measurement procedure. In this method, however, it is unsatisfactory that the regions amenable to the measurement should be limited to the outermost layer of the object of examination. For example, in a fruit as an object of such examination, the pericarp which constitutes the outermost layer is different from the sarcocarp in the interior of the fruit with respect to the structure of the tissue, and the composition, the related distribution, and the like of the chemical component. The determination of the sugar concentration in the sarcocarp necessitates relevant measurement at deeper positions than the outermost layer.

In U.S. Pat. No. 4,655,225 is described a prior art technique whereby sugars in human serum, especially glucose therein, can be quantitatively determined non-invasively. This technique, known as "incident angle modulation method", is a spectroscopic method wherein, in principle, a sample is irradiated with light beams from the outside and the light beams diffused and reflected from within the sample are spectroscopically analyzed. In this method the angle of incidence which light waves makes with a sample is changed. When this angle is small, the light beams penetrate deep underneath the outermost layer, and when the angle is large, the depth to which the light beam penetrates decreases. Therefore, by changing the depth to which a light beam penetrates underneath the outermost layer so as to find the respective spectral signals from the different depths, information from a deeper point, that is, the sugar concentration, can be discretely determined on the basis of the differential signal therebetween.

However, the above-mentioned prior art technique when practiced raises a problem in that the mechanism for modulating the angle of incidence is complicated on the one hand and the change in the incidence angle of light beam impairs the reproducibility under the influence of a resultant change in the reflection characteristic at the surface of the outer layer.

In said prior art method the light beam used for measurement are of wavelengths in the near infrared region, which are 2,270±15 nm, 2,100±15 nm, 1,765±15 mn, and 1,575±15 nm, and the reference wavelengths used are in the range of 1,000 to 2,700 nm. In order to enhance the accuracy of the measurement, however, shorter wavelengths in the near infrared region should be used for the measurement. The reason is that the liquid in a living body, especially in a fruit, agricultural product, or the like, consists of water in such a large proportion that the optical penetration depth of light beams to water, which assumes a larger degree on the side of shorter wavelengths, is of importance in the practice.

Wavelengths in the intermediate infrared range, especially those in the range of 7,500 to 15,000 nm called "fingerprint region", are effective in spectral analyses and have long since been used for identification and determination of organic compounds. Since, however, the water existing as a background exhibits such a high rate of absorption for said wavelength region that it is generally considered impractical to determine a specific component combined with water by the fingerprint region. Although light beams in visible region have a good optical penetrability in water, there exists no spectrum of a characteristic absorption bands for sugar in the visible light region.

SUMMARY OF THE INVENTION

Accordingly, an essential object of the present invention is to provide a spectroscopic measuring method, according to which the measuring apparatus can be made simpler than in the prior art and by using light beam of shorter wavelengths in the near infrared region the accuracy of the measurement can be enhanced.

Another object of the present invention is to provide an apparatus which is adapted to the practice of the above-mentioned method of this invention.

In accomplishing the above-mentioned objects there is provided, according to the present invention, a spectroscopic method for measuring the concentrations of sugars in samples, which comprises a first step wherein the light intensity of a light source in an interferometer is set at a first prescribed value and the outcoming light beam from said interferometer irradiate a sample placed in an integrating sphere, a second step wherein the diffusely reflected light from said sample collected by an integrating sphere is detected by a photo detector, a third step wherein the absorption spectrum of the sugar under measurement at a first depth in said sample is determined by processing the electrical signal from said photo detector by computer, a fourth step wherein the light intensity of the light source in said interferometer is set at a second prescribed value and the absorption spectrum of the sugar under measurement at a second depth in said sample is determined in the same manner as in said first, second and third steps, and a fifth step wherein the absorption spectrum of the sugar under measurement at a deeper region between said first and second depths in the sample is determined on the basis of the difference between the respective absorption spectrum determined in said third and fourth steps so that the concentration of the sugar under measurement in the deeper region in said sample can be determined on the basis of said absorption spectrum at the deeper region between said first and second depths, the wavelengths for the use for said absorption spectrum being selected from a wavelength band of from 950 to 1,150 nm, from 1,150 to 1,300 nm, or from 1,300 to 1,450 nm.

Since, according to the above-mentioned measuring method, the wavelengths selected for absorption spectrum are shorter and closer to the visible region than in the prior art methods, the light beam can penetrate deeper in the living tissue, and therefore, the region in the body tissue amenable to the measurement is widened beyond that in the prior art. Where the method of the present invention is used to determine the concentrations of sugars in the bloodstream in a human body, the selection of wavelengths from the wavelength bands specified above for the light beam enables them to reach the corium where capillaries are spread or to a point sufficiently close to the corium so that the measurement can be carried out non-invasively, that is, without taking out the sample blood.

Another advantage of this method is that the selection of wavelengths as specified above, that is, the use of shorter wavelengths which are closer to the visible region, for the light-throughput is increased, so that the efficiency of the apparatus can be improved and the accuracy of the measurement can be enhanced.

A further advantage of this method is that, since a technique of changing the light intensity of the light source is introduced so as to eliminate the background noise at the epidermal layer of the sample in measuring the concentrations of sugar at a depth beneath it as desired, the practice dispenses with a complicated apparatus such as a light beam incident angle modulator which was required in the prior art.

In accordance with the present invention, there is also provided a spectrophotometric apparatus for measuring the concentrations of sugar in samples, which comprises an interferometer wherein superposed light beams are emitted, a controller for adjusting the light intensity of the light source which is placed in said interferometer, an integrating sphere to collect diffusely reflected light from a sample placed at said integrating sphere, a photo detector for detecting said collected light and converting it into an electric signal, a processing means for processing the electric signal from said photo detector so as to compute the absorption spectrum of the sugar in said sample to be determined and for determining the concentration of the sugar under measurement on the basis of said absorption spectrum, and a means of selecting wavelengths for said absorption spectrum from a wavelength band of from 950 to 1,150 nm, from 1,150 to 1,300 nm, or from 1,300 to 1,450 nm. The processing means includes a means whereby, on the basis of the difference between the absorption spectrum of the sugar under measurement at a first depth in said sample which is computed for the light intensity of the light source in said interferometer set at a first prescribed value and the absorption spectrum of said sugar at a second depth which is computed for the light intensity of said source set at a second prescribed value, the absorption spectrum of the sugar under measurement at a deeper region between said first and second depths in said sample is computed and includes furthermore a means whereby, on the basis of said absorption spectrum at the deeper region between said first and second depths, the concentration of the sugar under measurement in the deeper region in the sample is computed.

BRIEF DESCRIPTION OF THE DRAWINGS

These and other objects and feature of the present invention will become apparent from the following description taken in conjunction with the preferred embodiment thereof with reference to the accompanying drawings, in which.

THE DETAILED DESCRIPTION OF THE INVENTION

The present invention will now be described in detail hereunder with reference to the accompanying drawings.

Figure 1:
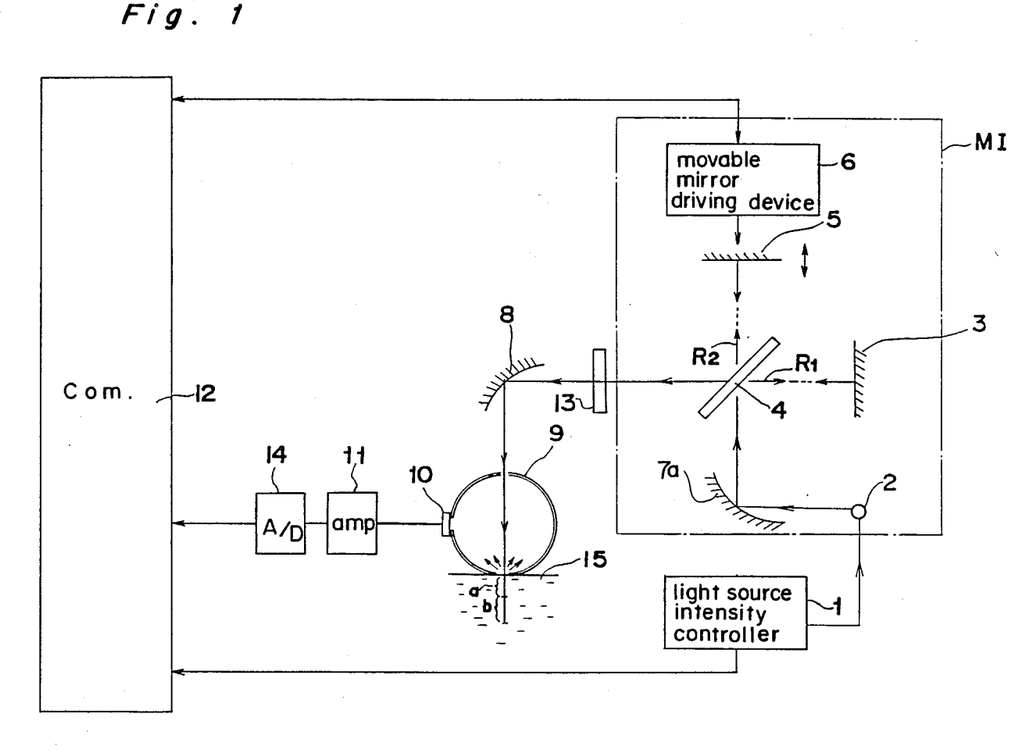
FIG. 1 schematically illustrates an apparatus used in the practice of the measuring method of the present invention.

Referring to FIG. 1, there is illustrated schematically an apparatus used in the practice of a measuring method embodying the present invention, which is as follows.

The illustration shows a Michelson type interferometer denoted by MI, which comprises a light source 2, a collimator 7a, i.e. a spherical reflecting mirror, which receives the light from said source 2 and reflects the parallel light beams, a beam splitter 4 that divides the collimated light beam into two beams $R_1$ and $R_2$ which makes a right angle to each other, one beam directed onto a fixed mirror 3 and the other onto a movable mirror 5. The beams reflected by said fixed mirror 3 and movable mirror 5 are recombined at said beam splitter 4. A movable mirror driving device 6 is arranged so as to move said movable mirror 5 to and fro. Here constructive and destructive interference occurs, depending on the position of the moving mirror 5 relative to the fixed mirror 3. The light intensity of the light source 2 can be adjusted by a light source intensity controller 1.

The outcoming light beam emitted from the Michelson type interferometer MI passes through a band-pass filter 13 which permits passage of the light beam of predetermined wavelength band. The light beams of a selected wavelength band are directed onto a spherical mirror 8 and reflected thereby into an integrating sphere 9 through the inlet provided therein so as to be focused onto a sample 15 placed at a window provided in the integrating sphere. The light beam penetrates the sample and is then diffusely reflected by the tissue underneath the epidermis and rise to the surface. The reflected light beam from the sample is collected by the integrating sphere and led to a detector 10, which is a photoelectric converter, placed at another window provided in the integrating sphere. The electrical signal produced by the detector 10 is amplified by an amplifier 11 and converted by an A/D converter into a digital signal, which is inputted to a computer 12. The signal, seen by the detector as a movable mirror scans to and fro, is the interfrogram.

A detailed explanation will now follow hereunder with respect to the wavelength region for the measurement which are selected by the band-pass filter 13.

As touched upon already, in the objects of measurement in the practice of the present invention, which are foods, fruits and other agricultural products, man, animals, and other creatures, the liquid in a living body subjected to the measurement consists of water in such a high proportion that it is essential to consider the absorption of light beam in water in the study of the application of the present invention.

Figure 2:
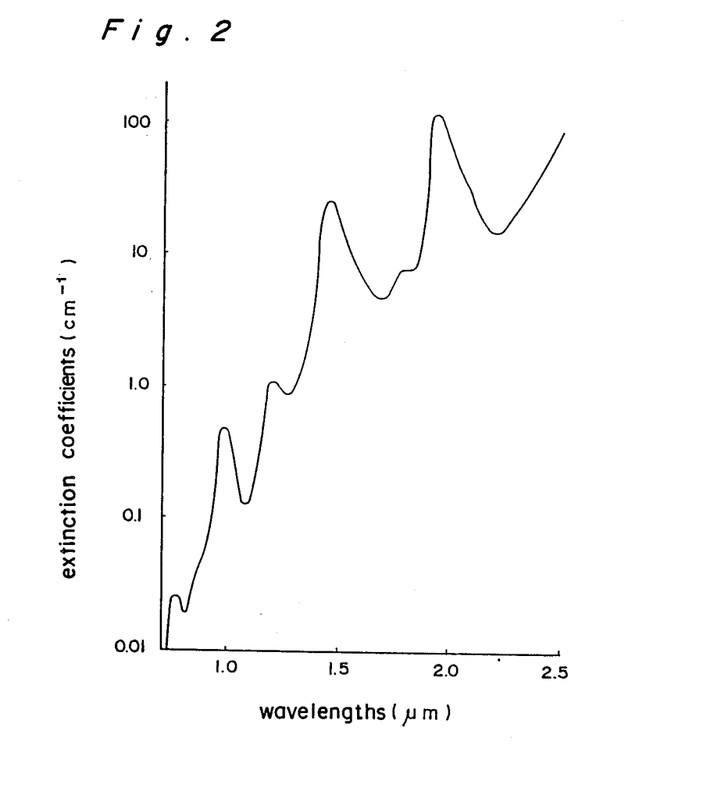
FIG. 2 shows the extinction coefficients of water in the near infrared region.

In FIG. 2 are shown extinction coefficients of water in the near infrared region. The extinction coefficients are shown along the axis of ordinate in relation to wavelengths taken on the axis of abscissas. As is clearly seen, the absorption of pure water is dependent upon the wavelength and have peaks around 1.93 $\mu$m, 1.43 $\mu$m, 1.15 $\mu$m, and 0.96 $\mu$m. And the depth of optical penetration to water is greater where the wavelength is shorter. The absorbance of water at a wavelength of 1.93 $\mu$m differs from that at 0.96 $\mu$m by about three to four orders of magnitude. Therefore, if a wavelength band is capable of determining the chemical component under examination, that is, the sugar, exists in the near infrared region closer to the visible region than the bands for measurement in the prior art, the use of the band enables the light beam to penetrate deeper into a water-containing living tissue and reach a point so deep as to show the chemical component at the value representative of the concentration at the region under investigation. It constitutes another advantage that the use of a wavelength band close to the visible region enhances the light-throughput and, therefore, results in improvement in efficiency of the measuring apparatus.

The present inventors, therefore, examined glucose and saccharose with respect to the feasibility of quantitatively determining each of them individually using wavelengths in the near infrared region, each of the two kinds of sugars closely resembling the other in molecular structure and their test as samples of sugars being of practical value. As a result, it was discovered that, although near infrared spectrum of glucose resemble those of saccharose so closely that spectrum of their mixture overlap and interfere, there existed bands of shorter wavelengths than in the prior art, with significant differences between the bands. Said band-pass filter 13 is designed to pass only the light beam in these specific wavelength bands.

A detailed description will follow hereunder with respect to light beam or spectrum in these significant bands.

Figure 3:
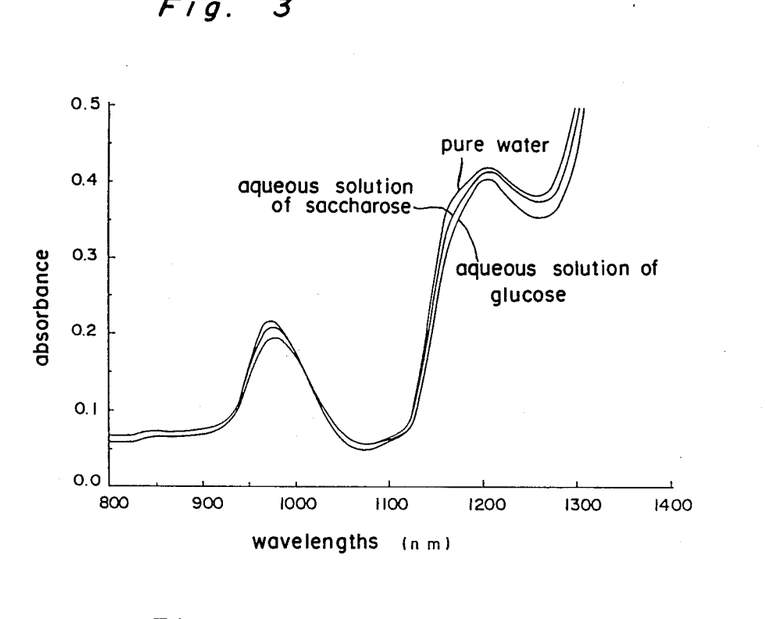
FIG. 3 shows absorbance spectrum of purified water, an aqueous solution of glucose, and an aqueous solution of saccharose.
Figure 4:
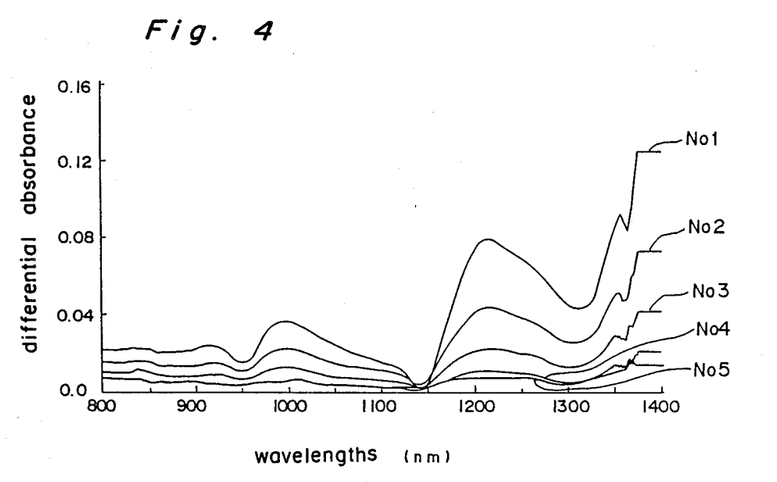
FIG. 4 shows differential spectrum between an aqueous solution of glucose and pure water.
Figure 5:
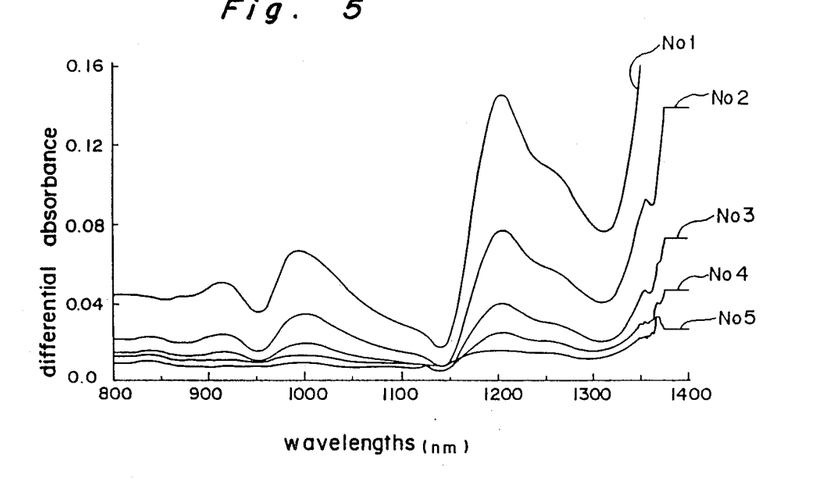
FIG. 5 shows the differential absorbance with respect to differential spectrum between an aqueous solution of saccharose and pure water.

When samples were aqueous solutions, as shown in FIG. 3, it was difficult to visually distinguish a significant difference in spectra between pure water and an aqueous solution of saccharose or an aqueous solution of glucose. The inventors then examined the differential spectrum between an aqueous solution of glucose and pure water (see FIG. 4) and those between an aqueous solution of saccharose and pure water (see FIG. 5). A differential spectrum herein means what remains after subtracting from a spectrum of an aqueous glucose or one of an aqueous saccharose the spectrum of pure water equivalent in quantity to the aqueous constituent of the aqueous glucose or the aqueous saccharose (this differential spectrum will hereinafter be referred to as a spectrum of pseudo-pure glucose or a spectrum of pseudo-pure saccharose). In FIGS. 4 and 5 the number assigned to each curve refers to the concentration of glucose or saccharose as follows:

No. 1: 2.0 Mol/l
No. 2: 1.0 Mol/l
No. 3: 0.5 Mol/l
No. 4: 0.25 Mol/l
No. 5: 0.125 Mol/l

Figure 6:
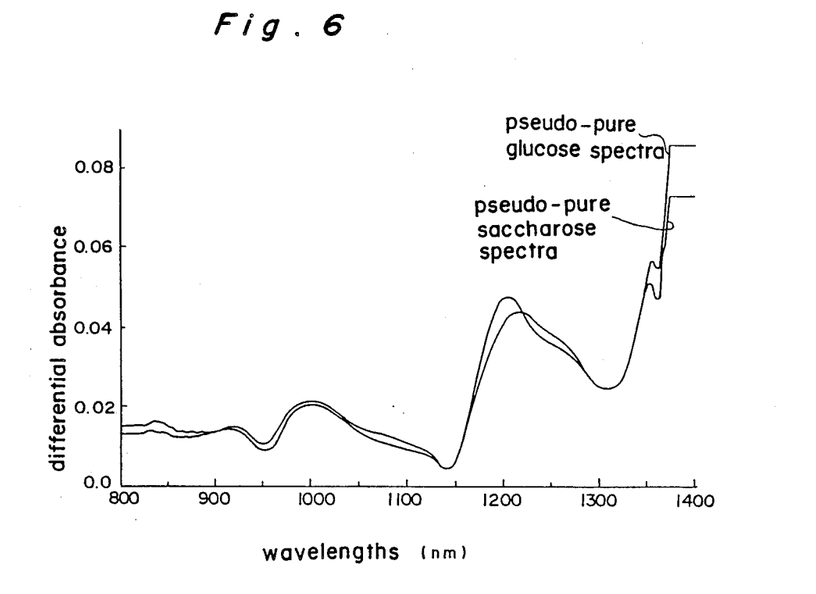
FIG. 6 shows differential absorbance between pseudo-pure glucose spectrum and pseudo-pure saccharose spectrum.
Figure 7:
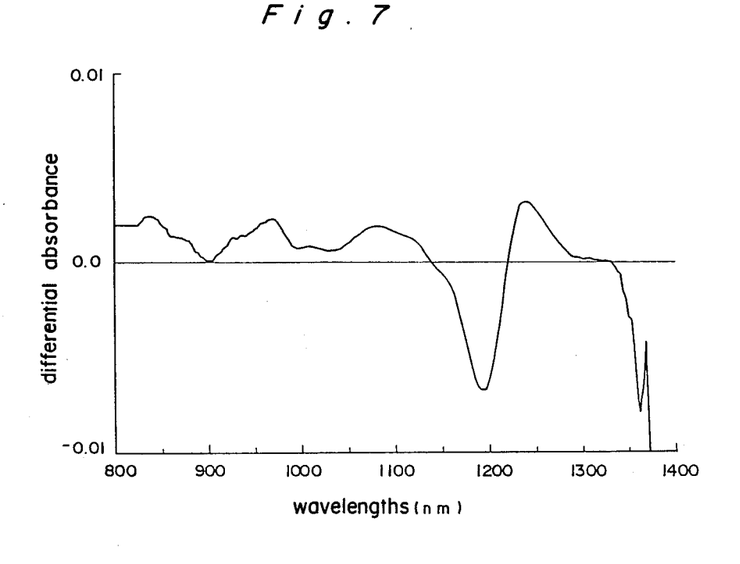
FIG. 7 shows the differential absorbance with respect to the differential spectrum between pseudo-pure glucose spectrum and pseudo-pure saccharose spectrum.

Then, to find the differences between the respective spectrum of glucose and saccharose, the spectrum of pseudo-pure glucose were compared with those of pseudo-pure saccharose, as shown in FIG. 6. The resultant differential spectrum (=pseudo-pure glucose spectrum - pseudo-pure saccharose spectrum) are shown in FIG. 7. As mentioned already, glucose and saccharose closely resemble each other in molecular structure and this fact is reflected in their spectrum, as shown in FIG. 6. Despite this similarity in molecular structure, however, significant difference can be observed in the wavelength bands of from 1,150 to 1,300 nm and from 950 to 1,150 nm.

Figure 8:
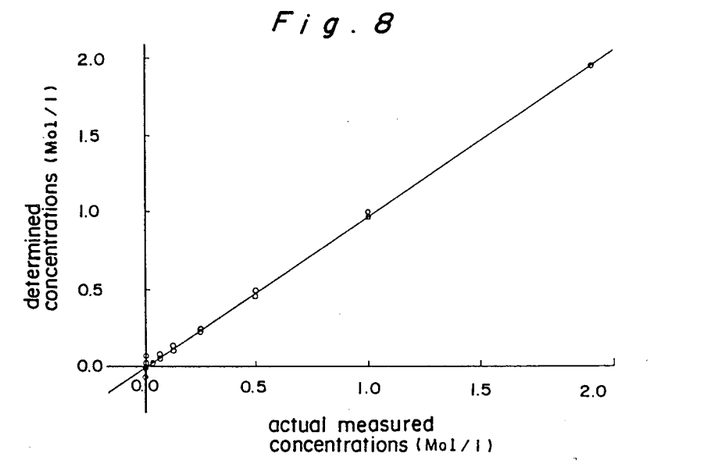
FIG. 8 shows the concentrations of glucose determined according to the invention, in relation to the actual measured concentrations, in the test using aqueous mixtures of glucose and saccharose wherein specific selected wavelengths were applied according to a model formula for determining glucose concentrations as described in the example that follows.
Figure 9:
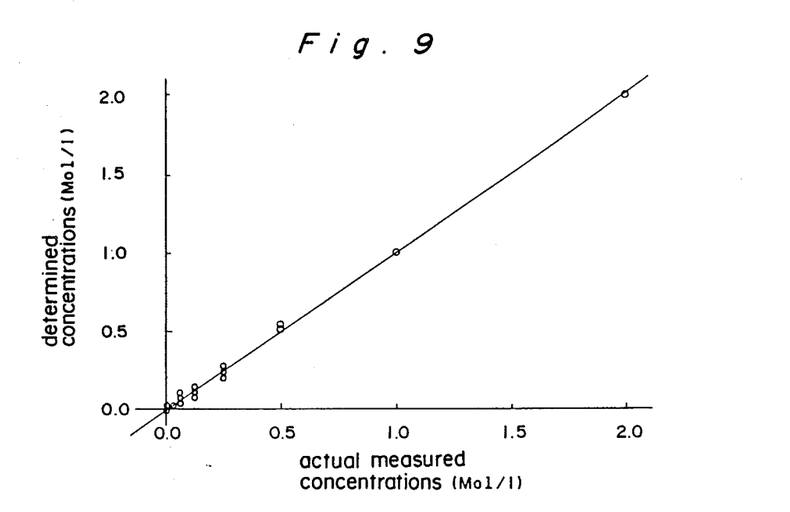
FIG. 9 shows the concentrations of saccharose determined according to the invention, in relation to the actual measured concentrations, in the test using aqueous mixtures of glucose and saccharose wherein a model formula for determining saccharose concentrations was used as described in the example that follows.

In a spectroscopic analysis of a three-component mixture consisting of glucose, saccharose and pure water, can be determined by introducing a mathematical formula using individually three specific wavelengths in said 1,150 to 1,300 nm band with significant differences observable therein, which are 1,230 nm at which the absorbance of glucose is conspicuous and relatively predominant, 1,205 nm at which the absorbance of saccharose is conspicuous and relatively predominant, and a base wavelength of 1,285 nm having no relevance to the concentrations of glucose and saccharose. By applying this method unknown samples were determined, FIGS. 8 and 9 showing the results. FIG. 8 relates to an aqueous solution mixture of glucose and saccharose and shows the concentrations determined by using a model formula for determining glucose concentrations, said determined concentrations shown along the axis of ordinate in relation to the actual measured concentrations (known concentrations) taken on the axis of abscissas.

The spectroscopic determination of the concentrations of components in a chemical system is based upon the Beer-Lambert law which states that the absorbance A is proportional to the concentration C (A=KC (K is a constant)). Even if it is assumed that the Beer-Lambert law can be expanded and applied to multi-component system, it is impossible to form a model formula or compute therewith unless all possible sets of components in the mixtures are specified. It is generally impracticable to prepare pure standard samples by specifying all possible sets of components especially in complex mixtures such as a living body.

On the other hand, the application of the inverse Beer-Lambert law (C=PA (C is a constant)), wherein the concentration C is regarded as a function of the absorbance A, enables a model to be formed and used in the computation in relation to specific components, that is, without the need of specifying all possible sets of components in a system. In other words, for example, a model formula can be formed for practical computation with respect to the concentration of glucose in a multicomponent system.

A model formula will be explained hereunder using a linear combination comprising, for example, absorbances at three different wavelengths.

$$C = \Sigma PiA(\lambda_i) + Po \qquad (1)$$
$$= P1A(\lambda 1) + P2A(\lambda 2) + P3A(\lambda 3) + Po$$

where $A(\lambda 1)$, $A(\lambda 2)$, and $A(\lambda 3)$ are the absorbances at selected wavelengths of $\lambda 1$, $\lambda 2$, and $\lambda 3$;

P1, P2, and P3 are proportional constants for the absorbances $A(\lambda i)$;

Po is an intercept term of the model.

The absorbance $A(\lambda i)$ at the selected optimum specific wavelength $\lambda i$ is divided into a component absorbance $Ag(\lambda i)$ depending on the concentration of glucose and a component absorbance $Ab(\lambda i)$ depending on the components other than glucose in the system.

$$A(\lambda i) = Ag(\lambda i) + Ab(\lambda i) \qquad (2)$$

$Ab(\lambda i)$ includes, besides the contribution from the sugar components other than glucose, the contribution from the background.

Then, by applying the equation (2) the equation (1) can be developed as follows:

$$\begin{aligned}C &= P1A(\lambda 1) + P2A(\lambda 2) + P3A(\lambda 3) + Po \qquad (3)\\ &= P1\{Ag(\lambda 1) + Ab(\lambda 1)\} + P2\{Ag(\lambda 2) + Ab(\lambda 2)\} +\\ &\quad P3\{Ag(\lambda 3) + Ab(\lambda 3)\} + Pgo + Pbo\\ &= \{P1Ag(\lambda 1) + P2Ag(\lambda 2) + P3Ag(\lambda 3) + Pgo\} +\\ &\quad \{P1Ab(\lambda 1) + P2Ab(\lambda 2) + P3Ab(\lambda 3) + Pbo\}\end{aligned}$$

Hence, $$Cg = \{P1Ag(\lambda 1) + P2Ag(\lambda 2) + P3Ag(\lambda 3) + Pgo\} \qquad (4)$$

and $$Cb = \{P1Ab(\lambda 1) + P2Ab(\lambda 2) + P3Ab(\lambda 3) + Pbo\} \qquad (5)$$

where Cg is a term depending on the glucose component and represents the true concentration of glucose; Cb represents the contribution from the components other than glucose and that from the background. Then, most optimum wavelengths $\lambda 1$, $\lambda 2$, and $\lambda 3$, optimum coefficients P1, P2, and P3, and Po are determined by multiregression in such a way as to satisfy $$Cb = P1Ab(\lambda 1) + P2Ab(\lambda 2) + P3Ab(\lambda 3) + Pbo \rightarrow 0 \qquad (6)$$

By thus canceling the contribution from the components other than glucose and that from the background, Cg representing the true concentration of glucose under investigation becomes obtainable in the model formula.

Since the equation (4) becomes almost equal to the equation (1), the concentration of glucose can be obtained by measuring the absorbances $A(\lambda 1)$, $A(\lambda 2)$, and $A(\lambda 3)$ at selected optimum wavelengths of $\lambda 1$, $\lambda 2$, and $\lambda 3$. Since the concentration of glucose is under investigation, the equation (1) is remodeled into $$Cg = Pg1A(\lambda 1) + Pg2A(\lambda 2) + Pg3A(\lambda 3) + Pgo \qquad (7)$$

The concentrations of the components other than glucose can be obtained in a manner similar to the above procedure.

A linear combination of absorbances at three wavelengths has been dealt with in explaining the model formula, but, without restricting the practice of this invention to this particular type of formulas, a model formula using absorbances at four wavelengths or more, doublet, or cross-product absorbance terms can be formed so as to be adapted to the accuracy required or particular cases of application.

An explanation will be given next with respect to the results of analysis obtained by using the equation (7) as a model formula.

Three selected specific optimum wavelengths in the band of 1,150–1,300 nm are $\lambda 1 = 1,205$ nm, $\lambda 2 = 1,230$ nm, and $\lambda 3 = 1,285$ nm. In FIG. 8, wherein the concentrations determined according to the invention are shown in relation to the actual measured concentrations, the straight line is the 45 degree on which all the points should lie in the absence of error. The marks "o" plotted therein, each representing the results obtained relating to a certain number of samples, lie along the straight line and shows that glucose can be individually determined by the use of said selected specific optimum wavelengths.

In a manner similar to the procedure for glucose mentioned above, saccharose can also be individually determined by using the three specific optimum wavelengths (1,205 nm, 1,230 nm, and 1,285 nm). FIG. 9 shows, with respect to aqueous mixtures of glucose and saccharose, the concentrations determined by using a model formula for determining concentrations of saccharose along the axis of ordinate in relation to the actual measured concentrations (previously known concentrations) taken on the axis of abscissas. The results obtained with respect to each sample lie around the straight line on which all the points should lie in the absence of error.

Similarly, glucose, saccharose and pure water in a three component system can each be individually determined by the use of three optimum wavelengths (950 nm, 980 nm, and 1,107 nm) in the band of from 950 to 1,150 nm where significant differences are shown.

Figure 10:
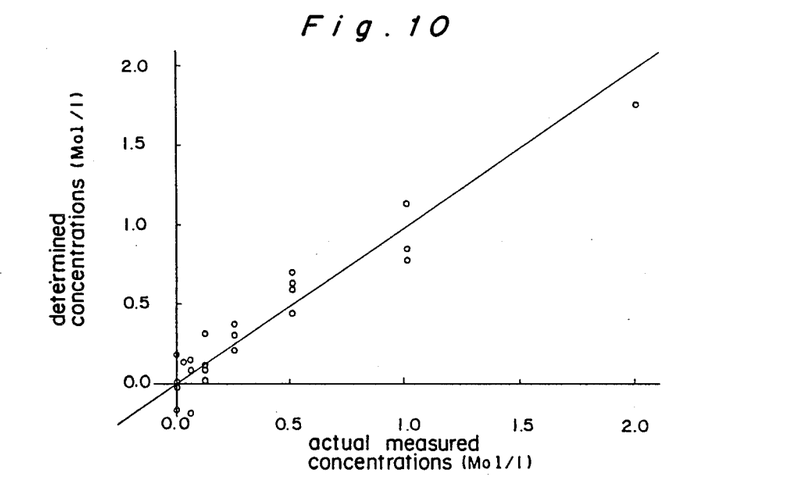
FIGS. 10 and 11 are the same representations as FIGS. 8 and 9 respectively, except that certain selected optimum wavelengths other than those specified in this invention were used.
Figure 11:
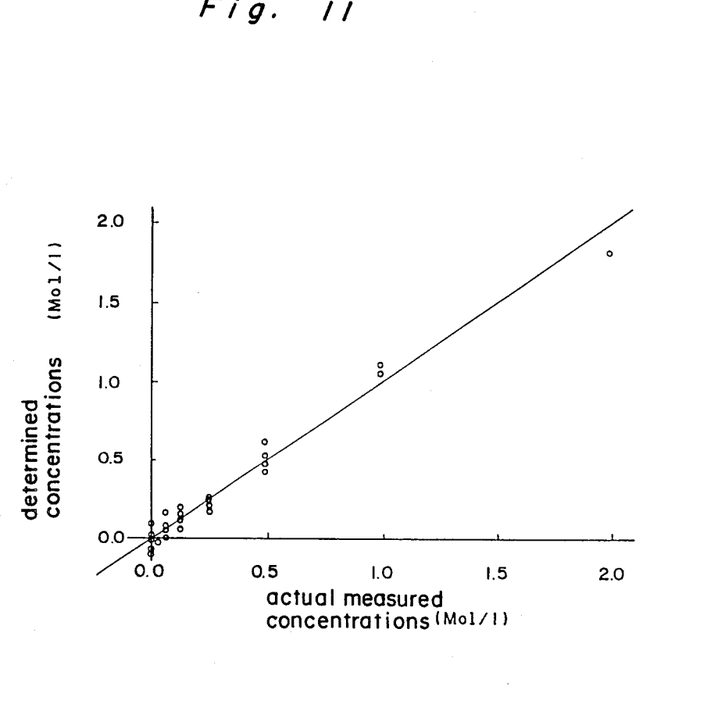

Also in the band of from 1,300 to 1,450 nm significant differences are seen in spectrum between glucose and saccharose (FIG. 7 shows this phenomenon only in part). Therefore, by using three optimum wavelengths (1,349 nm, 1,385 nm, and 1,400 nm) in this band each of said components can be separated in spectrum. In a manner similar to the above-mentioned example, analytical graphs were obtained mathematically with respect to unknown samples. The results in FIG. 10 (concentrations of glucose) and FIG. 11 (concentrations of saccharose) show better linearity in the relationship between the determined concentrations and the actual measured concentrations.

The wavelengths for the light beam used in the measuring apparatus in FIG. 1 are selected from any of the three wavelength bands, i.e., 950–1,150 nm, 1,150–1,300 nm, and 1,300–1,450 nm, as mentioned above.

Referring to FIG. 1, a detailed description will now follow with respect to the method of measurement of the concentrations of sugars in the tissue, particularly those of glucose as an example, at the depth b of the sample 15.

The first step begins with adjusting the light from the light source 2 to a prescribed intensity by means of the light source intensity controller 1 so as to examine the spectrum of the tissue at the outermost layer a of the sample. In other words, the light beams irradiating the sample 15 is so adjusted as to enter only the outermost layer a and be reflected back toward the outside. The spectrum pertaining to the outermost layer a of the sample 15 is then measured. The band-pass filter 13 then permits passage of the light beam of the necessary wavelength band, for example, in the range of 1,150–1,300 nm.

In the second step, the intensity of the light from the source is increased by the light source intensity controller 1 so as to enable the light beam from the interferometer MI sphere 9 to penetrate the sample 15 deeper to a depth b. In this way the spectrum of the sample 15 pertaining to both the outermost layer a and the deeper layer b are computed. For this deeper layer b, too, the computer 12 executes a program similar to that for the outermost layer a for the measurement.

In the third step, the computer 12 first computes the differential spectrum between the two spectrum obtained at the first step and the second step, secondly selects a number of wavelengths necessary for determining the concentration of the component under investigation, that is, the glucose, from said wavelength band of 1,150–1,300 nm, for example, three wavelengths of 1,205 nm, 1,230 nm, and 1,285 nm therefrom, and thirdly determines the concentration of glucose by introducing these selected wavelengths into a prescribed mathematical equation as hereinbefore described.

By following the above-mentioned spectrum procedure the background from the outermost layer a where glucose is not at all present or not contained to any significant degree can be eliminated and the concentration of glucose in the tissue at a deeper point b can be determined.

Although the present invention has been fully described by way of example with reference to the accompanying drawings, it is to be noted, here, that various changes and modifications will be apparent to those skilled in the art. Therefore, unless otherwise such changes and modifications depart from the scope of the present invention, they should be construed as included therein.

What is claimed is:

1. A spectroscopic method for measuring concentrations of sugars in samples, which comprises
    a first step wherein light intensity of a light source in an interferometer is set at a first prescribed value and outcoming light beams from said interferometer are emitted into an integrating sphere to irradiate a sample placed at a sample aperture of said integrating sphere,
    a second step wherein diffusely reflected light beams from said sample are detected by a photo detector,
    a third step wherein absorption spectrum of the sugar under measurement at a first depth in said sample is determined by processing electrical signals from said photo detector by a computer,
    a fourth step wherein the light intensity of the light source in said interferometer is set at a second prescribed value and absorption spectrum of the sugar under measurement at a second depth in said sample is determined in the same manner as in said first, second and third steps, and
    a fifth step wherein absorption spectrum of the sugar under measurement at a deeper region between said first and second depths in the sample is determined on the basis of the difference between the respective absorption spectrum determined in said third and fourth steps so that the concentration of the sugar under measurement in said deeper region in said sample can be determined on the basis of said absorption spectrum at said deeper region,
    the wavelengths for a use for said absorption spectrum being selected from a wavelength band of from 950 to 1,150 nm, from 1,150 to 1,300 nm, or from 1,300 to 1,450 nm.

2. A spectroscopic method as claimed in claim 1, wherein said wavelengths for the use for said absorption spectrum comprise three or more in number selected from any one of said wavelength bands.

3. A spectroscopic method as claimed in claim 1, wherein the sugar to be determined is selected from a group of glucose, saccharose, and fructose.

4. A spectroscopic method as claimed in claim 1, wherein the sugar to be determined is a sugar in human blood.

5. A spectrophotometric apparatus for measuring concentrations of sugars in samples, which comprises
    an interferometer for emitting superposed light beams,
    a controller for adjusting light intensity of a light source which is placed in said interferometer,
    an integrating sphere for collecting diffusely reflected light beams from a sample placed at said integrating sphere,
    a photo detector for detecting said collected light and converting it into an electric signal,
    a processing means for processing electric signal from said photo detector so as to compute absorption spectrum of the sugar in said sample to be determined and for determining the concentration of the sugar under measurement on the basis of said absorption spectrum, and
    a means for selecting optimum wavelengths for a use for said absorption spectrum from a wavelength band of 950 to 1,150 nm, from 1,150 to 1,300 nm, or from 1,300 to 1,450 nm,
    said processing means including a means whereby, on the basis of the difference between the absorption spectrum of the sugar under measurement at a first depth in said sample which is computed for light intensity of said light source in said interferometer set at a first prescribed value and absorption spectrum of said sugar at a second depth which is computed for light intensity of said source set at a second prescribed value, the absorption spectrum of the sugar under measurement at a deeper region between said first and second depths in said sample is computed and including furthermore a means whereby, on the basis of said absorption spectrum at said deeper region, the concentration of the sugar under measurement in said deeper region in the sample is computed.

* * * * *